United States Patent
Giles et al.

(10) Patent No.: US 10,662,454 B2
(45) Date of Patent: May 26, 2020

(54) LIGNOCELLULOSIC TREATMENTS AND APPLICATIONS THEREOF

(75) Inventors: Richard Giles, Lincolnton, NC (US); Matthew Parrow, Charlotte, NC (US)

(73) Assignee: University of North Carolina at Charlotte, Charlotte, NC (US)

( * ) Notice: Subject to any disclaimer, the term of this patent is extended or adjusted under 35 U.S.C. 154(b) by 0 days.

(21) Appl. No.: 13/116,860

(22) Filed: May 26, 2011

(65) Prior Publication Data

US 2011/0294169 A1    Dec. 1, 2011

Related U.S. Application Data

(60) Provisional application No. 61/348,278, filed on May 26, 2010.

(51) Int. Cl.
| | | |
|---|---|---|
| C12P 19/02 | (2006.01) | |
| C12P 19/04 | (2006.01) | |
| C12P 7/10 | (2006.01) | |
| C12R 1/645 | (2006.01) | |
| C12P 19/14 | (2006.01) | |
| C12P 39/00 | (2006.01) | |
| C08H 8/00 | (2010.01) | |

(52) U.S. Cl.
CPC ............... *C12P 19/02* (2013.01); *C08H 8/00* (2013.01); *C12P 7/10* (2013.01); *C12P 19/04* (2013.01); *C12P 19/14* (2013.01); *C12P 39/00* (2013.01); *C12R 1/645* (2013.01); *Y02E 50/16* (2013.01)

(58) Field of Classification Search
None
See application file for complete search history.

(56) References Cited

U.S. PATENT DOCUMENTS

| | | | | |
|---|---|---|---|---|
| 5,460,697 A | * | 10/1995 | Akhtar et al. | 162/72 |
| 2010/0248320 A1 | * | 9/2010 | Lyons et al. | 435/165 |
| 2015/0010989 A1 | * | 1/2015 | Medoff | C08H 8/00 |
| | | | | 435/277 |

OTHER PUBLICATIONS

Terhi Hakala, Characterization of the lignin-modifying enzymes of the selective white-rot fungus physisporinus rivulosus, Thesis, University of Helsinki, Oct. 19, 2007.*
Filley et al. Lignin demethylation and polysaccharide decomposition in spruce sapwood degraded by brown rot fungi, Organic geochemistry (2002), 33: 111-124.*
W. Zimmermann, Degradation of lignin by bacteria, Journal of Biotechnology (1990), 13: 119-130.*
Valjamae et al. Acid hydrolysis of bacterial cellulose reveals different modes of synergistic action between cellobiohydrolase I and endoglucanase I, Eur J. Biochem (1999), 266: 327-334.*
Hasan et al. The influence of sterilization by gamma radiation on natural durability of wood, Wood Research 53(4): 23-34, 2008).*

* cited by examiner

*Primary Examiner* — Iqbal H Chowdhury
(74) *Attorney, Agent, or Firm* — J. Clinton Wimbish; Nexsen Pruet, PLLC (57) ABSTRACT

In one aspect, methods of treating lignocellulosic materials are described herein. In some embodiments, a method of treating a lignocellulosic material comprises degrading lignin of the lignocellulosic material with at least one fungus and hydrolyzing cellulose of the lignocellulosic material with at least one microorganism.

14 Claims, 2 Drawing Sheets

LIGNOCELLULOSIC TREATMENTS AND APPLICATIONS THEREOF

RELATED APPLICATION DATA

The present application hereby claims priority pursuant to 35 U.S.C. § 119(e) to U.S. Provisional Patent Application Ser. No. 61/348,278, filed May 26, 2010, which is hereby incorporated by reference in its entirety.

FIELD OF THE INVENTION

The present invention relates to treatments for decomposing lignocellulosic materials and, in particular, to the use of whole microorganisms in the decomposition process.

BACKGROUND

Lignocellulosic materials are widely abundant sparking considerable interest in these materials for various biofuel applications. Lignocellulosic biomass such as wood waste, crop stalks and grasses are potentially sustainable sources of biomass for ethanol production. With most of the terrestrial biomass on earth being lignocellulosic, producing ethanol from lignocellulosic material has the potential to replace up to 30% of annual petroleum consumption in the United States while significantly reducing greenhouse gas emissions. Moreover, the use of lignocellulosic material in ethanol production does not encounter food production pressures as with other crop sources for ethanol such as corn.

Nevertheless, the abundant sugars contained in lignocellulosic materials are blocked from traditional ethanol-producing fermentation reactions because they typically occur in a complex polymerization of lignin and celluloses that is difficult to hydrolyze into soluble sugars for fermentation. Since lignin is highly resistant to water penetration and enzymatic breakdown, it represents a significant barrier to isolating cellulose and other sugars for use in production of both paper and ethanol biofuel. Similarly, the high degree of polymerization of cellulose in woody biomass is also a significant barrier to efficient biofuel conversion and requires chemical and/or enzymatic hydrolysis to produce soluble sugars for fermentation.

Current methods using chemical and enzymatic processes for lignin removal and cellulose hydrolysis are cost prohibitive and inefficient to support industrial-scale lignocellulosic ethanol production. Such chemical and enzymatic processes include harsh liquid-phase acid or base-catalyzed pretreatments aimed at making the cellulose more accessible to enzymatic hydrolysis. These chemical treatments additionally require specialized facilities for safely handling and disposing of hazardous chemicals, resulting in increased costs and environmental concerns. Furthermore, current enzymatic cellulose hydrolysis processes use expensive extracted and purified cellulase enzymes applied to the lignocellulosic biomass in liquid-phase batches. As a result of these significant processing drawbacks, commercially viable ethanol production from lignocellulosic materials remains unrealized.

SUMMARY

In one aspect, methods of treating lignocellulosic materials are described herein. In some embodiments, a method of treating lignocellulosic materials described herein can overcome one or more of the foregoing disadvantages of using lignocellulosic materials in the production of ethanol.

In some embodiments, a method of treating a lignocellulosic material comprises degrading lignin of the lignocellulosic material with at least one fungus and hydrolyzing cellulose of the lignocellulosic material with at least one microorganism. In some embodiments, lignin is selectively degraded by the at least one fungus. In some embodiments, the at least one fungus comprises a white rot fungus. In some embodiments, the at least one fungus comprises a plurality of fungi. The plurality of fungi, in some embodiments, comprises white rot fungi.

In some embodiments, the at least one cellulose hydrolytic microorganism of the treatment comprises at least one fungus. In some embodiments, for example, a microorganism comprises a brown rot fungus. The at least one microorganism, in some embodiments, comprises a plurality of fungi. In some embodiments, a plurality of fungi serving as the cellulose hydrolytic microorganism comprises brown rot fungi. Alternatively, a microorganism, in some embodiments, comprises one or more cellulose-hydrolytic bacteria. In some embodiments, the at least one microorganism comprises a combination of fungus and cellulose-hydrolytic bacteria.

In some embodiments, a lignin degrading fungus is applied to the lignocellulosic material prior to application of the at least one cellulose hydrolytic microorganism. In some embodiments, the microorganism is applied to the lignocellulosic material prior to application of a lignin degrading fungus. In some embodiments, a lignin degrading fungus and a microorganism are applied to the lignocellulosic material simultaneously or substantially simultaneously.

In some embodiments wherein a lignin degrading fungus is applied to the lignocellulosic material, the lignocellulosic material is sterilized or substantially sterilized prior to application of the at least one cellulose hydrolytic microorganism. In some embodiments, for example, a lignin selective white rot fungus is applied to the lignocellulosic material for a desired period of time. The lignocellulosic material is subsequently sterilized or substantially sterilized prior to application of a microorganism, such as a brown rot fungus, for the hydrolysis of cellulose of the lignocellulosic material.

In some embodiments, the lignocellulosic material is not sterilized prior to application of the at least one microorganism such that the lignin degrading fungus and the cellulose hydrolytic microorganism exist simultaneously on the lignocellulosic material.

In some embodiments, a lignin selective fungus or fungi for use in one or more methods described herein degrades at least a portion of lignin of the lignocellulosic material without degrading or substantially degrading cellulose of the lignocellulosic material. In some embodiments, a lignin selective fungus degrades all or substantially all of the lignin of the lignocellulosic material without degrading or substantially degrading cellulose of the lignocellulosic material. In some embodiments, degradation of the lignin provides increased access to the cellulose and/or hemicellulose of the lignocellulosic material for hydrolysis by the microorganism.

In another aspect, methods of producing ethanol are described herein. In some embodiments, a method of producing ethanol comprises providing a lignocellulosic material, degrading lignin of the lignocellulosic material with at least one fungus, hydrolyzing cellulose of the lignocellulosic material with at least one microorganism, further hydrolyzing the cellulose with one or more cellulase enzymes into one or more fermentable sugars and fermenting the one or more sugars into ethanol.

In some embodiments, the lignin of the lignocellulosic material is selectively degraded by the at least one fungus. In some embodiments of methods of producing ethanol, the at least one fungus comprises a white rot fungus. In some embodiments, the at least one fungus comprises a plurality of fungi. The plurality of fungi, in some embodiments, comprises white rot fungi.

In some embodiments, the at least one cellulose hydrolytic microorganism of a method of producing ethanol comprises at least one fungus. In some embodiments, for example, a microorganism comprises a brown rot fungus. The at least one microorganism, in some embodiments, comprises a plurality of fungi. In some embodiments, a plurality of fungi serving as the cellulose hydrolytic microorganism comprises brown rot fungi. Alternatively, a microorganism, in some embodiments, comprises one or more cellulose hydrolytic bacteria. In some embodiments, the at least one microorganism comprises a combination of fungus and cellulose hydrolytic bacteria.

In some embodiments of producing ethanol, a lignin degrading fungus is applied to the lignocellulosic material prior to application of the at least one microorganism. In some embodiments, the microorganism is applied to the lignocellulosic material prior to application of a lignin degrading fungus. In some embodiments, a lignin degrading fungus and a cellulose hydrolytic microorganism are applied to the lignocellulosic material simultaneously or substantially simultaneously.

In some embodiments of producing ethanol wherein a lignin degrading fungus is applied to the lignocellulosic material prior to application of at least one microorganism, the lignocelluosic material is sterilized or substantially sterilized prior to application of the at least one microorganism. In some embodiments, for example, a lignin selective white rot fungus is applied to the lignocellulosic material for a desired period of time. The lignocellulosic material is subsequently sterilized or substantially sterilized prior to application of a microorganism, such as a brown rot fungus, for the hydrolysis of cellulose of the lignocellulose material.

In some embodiments, the lignocellulosic material is not sterilized prior to application of the at least one microorganism such that the lignin degrading fungus and the cellulose hydrolytic microorganism exist simultaneously on the lignocellulosic material.

In some embodiments of producing ethanol, a lignin selective fungus or fungi degrades at least a portion of lignin of the lignocellulosic material without degrading or substantially degrading cellulose of the lignocellulosic material. In some embodiments, a lignin selective fungus or fungi degrades all or substantially all of the lignin of the lignocellulosic material without degrading or substantially degrading cellulose of the lignocellulosic material.

In some embodiments, degradation of the lignin provides increased access to the cellulose and/or hemicellulose of the lignocellulosic material for hydrolysis by the microorganism and one or more cellulase enzymes. As described further herein, hydrolysis of cellulose by the microorganism and one or more cellulase enzymes can produce sugars suitable for fermentation into ethanol by techniques known to one of skill in the art. In some embodiments of producing ethanol, sugars produced according to methods described herein comprise hexoses, pentoses and/or mixtures thereof. In some embodiments, hexoses comprise glucose, mannose or galactose or mixtures thereof. In some embodiments, pentoses comprise xylose or arabinose or mixtures thereof.

In another aspect, bioreactors for treating lignocellulosic material are described herein. In some embodiments, a bioreactor comprises a container for storing lignocellulosic material and apparatus for introducing at least one lignin degrading fungus and at least one cellulose-hydrolytic microorganism to the lignocellulosic material in the container. In some embodiments, a lignin degrading fungus and cellulose-hydrolytic microorganism introduced to the lignocellulosic material through the apparatus of the bioreactor can comprises any of the same described herein.

Moreover, in some embodiments, a bioreactor described herein further comprises one or more agitators for mixing or mechanically agitating the lignocellulosic material in the container. Additionally, in some embodiments, a bioreactor described herein comprises apparatus suitable for autoclaving or otherwise sterilizing the lignocellulosic material in the container.

These and other embodiments are described in further detail in the detailed description which follows.

DETAILED DESCRIPTION

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

In one aspect, methods of treating lignocellulosic materials are described herein. In some embodiments, a method of treating a lignocellulosic material comprises degrading lignin of the lignocellulosic material with at least one fungus and hydrolyzing cellulose of the lignocellulosic material with at least one microorganism. In some embodiments, lignin is selectively degraded by the at least one fungus.

Turning now to components of methods described herein, a method described herein comprises a lignocellulosic material. Any desired lignocellulosic material not inconsistent with objectives of the present invention can be used. In some embodiments, a lignocellulosic material comprises one or more types of wood. In some embodiments, for example, wood comprises one or more types of hardwood, softwood or mixtures thereof. In some embodiments, wood comprises one or more types of genetically modified woods or plants. In some embodiments, a lignocellulosic material comprises plant leaves and/or stalks including, but not limited to, corn stover. Moreover, in some embodiments, lignocellulosic material comprises one or more grasses including, but not limited to, switchgrass. Lignocellulosic material suitable for use in methods described herein, in some embodiments can be obtained as waste products from various applications such as timber harvesting and associated processing, agricultural harvesting and associated processing and/or landscape clearing and maintenance applications.

In some embodiments, a lignocellulosic material suitable for use in one or more methods described herein has a moisture content of at least about 10%. In some embodiments, a lignocellulosic material has a moisture content of at least about 15% or at least about 20%. A lignocellulosic material, in some embodiments, has a moisture content of at least about 30% or at least about 50%. In some embodiments, a lignocellulosic material has a moisture content ranging from about 10% to about 80% or from about 20% to about 60%. In some embodiments, moisture can be added to the lignocellulosic material prior to a treatment described herein.

In some embodiments, a lignocellulosic material is provided in particulate form. In some embodiments, for example, wood is provided in particulate form for administering a method described herein. In some embodiments, wood and/or other forms of lignocellulosic material can be chipped or ground into particulate form in preparation for administering a method described herein.

In addition to a lignocellulosic material, methods described herein comprise at least one fungus for degrading lignin of the lignocellulosic material. In some embodiments, the at least one fungus is operable to degrade lignin and cellulose of the lignocellulosic material. In some embodiments, for example, a lignin and cellulose degrading fungus comprises one or more simultaneous white rot fungi.

In some embodiments, the at least one fungus selectively degrades lignin of the lignocellulosic material. A lignin selective fungus, in some embodiments, for example, comprises a white rot fungus. Moreover, in some embodiments, the at least one fungus comprises a plurality of fungi. The plurality of fungi, in some embodiments, comprises lignin selective white rot fungi. Suitable white rot fungus or fungi can be selected according to several factors including the identity/type of lignocellulosic material provided, the moisture content and/or temperature of the lignocellulosic material and/or environment in which the method is administered. In some embodiments, suitable lignin selective white rot fungus or fungi are selected from any of the same listed in Table I herein.

TABLE I

Lignin Selective White Rot Fungi

Bjerkandera adusta (Polyporus adustus)
Ceriporiopsis subvermispora
Cerrena unicolor (Daedalea unicolor)
Dichomitus squalens (Polyporus anceps)
Dichomitus squalens
Dichomitus squalens FP 58543
Dichomitus squalens FP 100565
Dichomitus squalens FP 313
Ganoderma applanatum
Ganoderma lobatum FP 18692
Ganoderma lobatum FP 18679
Ganoderma oregonense
Ganoderma tsugae
Hapalopilus croceus (Polyporus croceus) FP 46228
Hapalopilus croceus FP 12503
Heterobasidion annosum (Fomes annosus)
Heterobasidion annosum
Inonotus dryadeus FP 36133
Inonotus dryophilus (Polyporus dryophilus)
Inonotus dryophilus
Inonotus ludovicianus FP 18695
Inonotus rheades Strid-1076
Inonotus texanus FP 94178
Inonotus tomentosus
Ischnoderma resinosum
Laurillia sulcata (Stereum sulcatum) FP 105104
Perenniporia medulla-panis (Poria medulla-panis)

TABLE I-continued

Lignin Selective White Rot Fungi

Perenniporia subacida (Poria subacida)
Perenniporia subacida FP 94346
Phellinus sp.
Phellinus fastuosus FP 21778
Phellinus nigrolimitatus (Fomes nigrolimitatus)
Phellinus nigrolimitatus
Phellinus pini
Phellinus viticola (P. isabellinus) FP 4250
Phlebia tremellosa
Scytinostroma galactinium
Xylobolus frustulatus (Stereum frustulatum)
Xylobolus frustulatus
Xylobolus subpileatus (Stereum subpileatum) FP 18502
Xylobolus subpileatus FP 12703

In some embodiments, any combination of white rot fungi of Table I can be used in a method described herein as determined according to the specific parameters of the method, including lignocellulosic material type and treatment environment.

In some embodiments, a lignin selective fungus or fungi for use in one or more methods described herein degrades at least a portion of lignin of the lignocellulosic material without degrading or substantially degrading cellulose of the lignocellulosic material. In some embodiments, a lignin selective fungus degrades all or substantially all of the lignin of the lignocellulosic material without degrading or substantially degrading cellulose of the lignocellulosic material. In some embodiments, degradation of the lignin provides increased access to the cellulose and/or hemicellulose of the lignocellulosic material for hydrolysis by the microorganism.

In addition to at least one lignin degrading fungus, methods described herein, in some embodiments, comprise at least one microorganism operable to hydrolyze cellulose of the lignocellulosic material. In some embodiments, the at least one cellulose hydrolytic microorganism comprises at least one fungus. In some embodiments, for example, a microorganism comprises a brown rot fungus. The at least one microorganism, in some embodiments, comprises a plurality of fungi. In some embodiments, a plurality of fungi serving as the cellulose hydrolytic microorganism comprises brown rot fungi. Suitable brown rot fungus or fungi can be selected according to several factors including the identity/type of lignocellulosic material provided, the moisture content and/or temperature of the lignocellulosic material and/or environment in which the method is administered. In some embodiments, suitable brown rot fungus or fungi are selected from any of the same listed in Table II herein.

TABLE II

Brown Rot Fungi

Coniophora prasinoides
Coniophora puteana
Fomitopsis pinicola
Gloeophlyllum trabeum
Laetiporus sulphureus
Leucogyrophana arizonica
Lentinus lepidius
Piptoporus betulinus
Poria placenta
Posita placenta
Tyromyces balsameus In some embodiments, any combination of brown rot fungi of Table II can be used in a method described herein as determined according to the specific parameters of the method, including lignocellulosic material type and treatment environment.

Alternatively, in some embodiments, a microorganism comprises one or more cellulose hydrolytic bacteria. In some embodiments, a microorganism comprises one or more cellulose hydrolytic bacteria of Table III.

TABLE III

Cellulose Hydrolytic Bacteria

Aerobic bacteria

Cellulomonas flavigena
C. biazotea
C. cellasea
C. fimi
C. gelida
C. cartae
C. uda
C. turbata
Bacillus brevis
B. firmus
B. lichenformis
B. pumilus
B. subtilis
B. polymyxa
B. cerus
Serrata marcescens
Heretosiphon geysericolus
Sporocytophaga myxococcoides
Streptomyces flavogriseus
Thermoonsopora curvata Anaerobic bacteria Acetivibrio cellulolyticus
Clostridium cellobioparum
C. papyrosolvens
C. stercorarium
C. acetobutylicum
Bacteroides succinogenes
Butyrivibrio fibrisolvens
Ruminococcus albus
R. flavefaciens
Eubacterium cellusolvens
Micromonospora ruminantiurn
M. propionici In some embodiments, the at least one microorganism comprises a combination of fungus and cellulose-hydrolytic bacteria.

In some embodiments of methods described herein, a lignin degrading fungus is applied to the lignocellulosic material prior to application of the at least one microorganism. Lignin degrading fungus or fungi can be applied to the lignocellulosic material for any desired period of time prior to application of the at least one cellulose hydrolytic microorganism. In some embodiments, for example, a lignin degrading fungus is applied to the lignocellulosic material for a time period sufficient to degrade a desired amount of lignin.

The time period over which a lignin degrading fungus is applied to a lignocellulosic material can be dependent on several factors including the identity of the fungus, identity of the lignocellulosic material, amount of the lignocellulosic material and/or the surrounding environmental conditions. In some embodiments, for example, a lignin degrading fungus is applied to the lignocellulosic material for a time period of at least about 1 week. In some embodiments, a lignin degrading fungus is applied to the lignocellulosic material for a time period of at least about 2 weeks or at least about 3 weeks. In some embodiments, a lignin degrading fungus is applied to the lignocellulosic material for a time period ranging from about 1 week to about 5 weeks. In some embodiments, a lignin degrading fungus is applied to the lignocellulosic material for a time period ranging from about 2 weeks to about 4 weeks. In some embodiments, a lignin degrading fungus is applied to the lignocellulosic material for a time period less than about 1 week.

In some embodiments, a lignin degrading fungus or fungi is operable to degrade at least about 1 weight percent of the lignin content of the lignocellulosic material. In some embodiments, a lignin degrading fungus or fungi degrades at least about 5 weight percent or at least about 10 weight percent of the lignin content of the lignocellulosic material. In some embodiments, a lignin degrading fungus or fungi degrades at least about 25 weight percent or at least about 50 weight percent of the lignin content of the lignocellulosic material. In some embodiments, a lignin degrading fungus or fungi degrades from about 1 weight percent to about 90 weight percent of the lignin content of the lignocellulosic material. In some embodiments, a lignin degrading fungus or fungi degrades from about 5 weight percent to about 75 weight percent of the lignin content of the lignocellulosic material. In some embodiments, a lignin degrading fungus or fungi degrades from about 10 weight percent to 60 weight percent of the lignin content of the lignocellulosic material. Moreover, as described herein, a lignin degrading fungus or fungi, in some embodiments, can selectively degrade lignin of the lignocellulosic material in any of the foregoing amounts without degrading or substantially degrading the cellulose content of the lignocellulosic material.

In some embodiments wherein a lignin degrading fungus is applied to the lignocellulosic material, the lignocellulosic material is sterilized or substantially sterilized prior to application of the at least one microorganism. In some embodiments, the lignocellulosic material treated with the at least one lignin degrading fungus can be sterilized with steam or through various autoclaving techniques. In some embodiments, for example, a lignin selective white rot fungus is applied to the lignocellulosic material for a desired period of time. The lignocellulosic material is sterilized or substantially sterilized prior to application a microorganism, such as a brown rot fungus, for the hydrolysis of cellulose of the lignocellulosic material.

Alternatively, in some embodiments, the lignocellulosic material is not sterilized prior to application of the at least one microorganism such that the lignin degrading fungus and the cellulose hydrolytic microorganism exist simultaneously on the lignocellulosic material.

In some embodiments, the at least one microorganism can be applied to the lignocellulosic material prior to application of the at least one lignin degrading fungus. In some embodiments, the lignocellulosic material comprising the microorganism is sterilized or substantially sterilized prior to application of a lignin degrading fungus. In some embodiments, the lignocellulosic material is not sterilized prior to application of a lignin degrading fungus such that the lignin degrading fungus and cellulose hydrolytic microorganism exist simultaneously on the lignocellulosic material.

Additionally, in some embodiments, a lignin degrading fungus and a cellulose hydrolytic microorganism are applied to the lignocellulosic material simultaneously or substantially simultaneously.

A cellulose hydrolytic microorganism can be applied to the lignocellulosic material for any desired period of time. In some embodiments, for example, a cellulose hydrolytic microorganism is applied to the lignocellulosic material for a time period sufficient to hydrolyze a desired amount of cellulose and/or hemicellulose.

The time period over which a cellulose hydrolytic microorganism is applied to a lignocellulosic material can be dependent on several factors including the identity of the microorganism, identity of the lignocellulosic material, amount of the lignocellulosic material and/or the surrounding environmental conditions. In some embodiments, for example, a cellulose hydrolytic microorganism is applied to the lignocellulosic material for a time period of at least about 1 week. In some embodiments, a cellulose hydrolytic microorganism is applied to the lignocellulosic material for a time period of at least about 2 weeks or at least about 3 weeks. In some embodiments, a cellulose hydrolytic microorganism is applied to the lignocellulosic material for a time period ranging from about 1 week to about 5 weeks. In some embodiments, a cellulose hydrolytic microorganism is applied to the lignocellulosic material for a time period ranging from about 2 weeks to about 4 weeks. In some embodiments, a cellulose hydrolytic microorganism is applied to the lignocellulosic material for a time period less than about 1 week.

In some embodiments, the cellulose hydrolytic microorganism is operable to depolymerize cellulose and/or hemicellulose of the lignocellulosic material into shorter polysaccharides, oligosaccharides or monomeric sugars or mixtures thereof. In some embodiments, a cellulose hydrolytic microorganism depolymerizes cellulose of the lignocellulosic material into polysaccharides and/or oligosaccharides having an average chain length of up to about 1000. In some embodiments, a cellulose hydrolytic microorganism depolymerizes cellulose of the lignocellulosic material into polysaccharides and/or oligosaccharides having an average chain length of up to about 700 or up to about 500. In some embodiments, a cellulose hydrolytic microorganism depolymerizes cellulose of the lignocellulosic material into polysaccharides and/or oligosaccharides having an average chain length of up to about 400 or up to about 300.

In some embodiments, a cellulose hydrolytic microorganism depolymerizes cellulose of the lignocellulosic material into polysaccharides and/or oligosaccharides having an average chain length ranging from about 10 to about 1000. In some embodiments, a cellulose hydrolytic microorganism depolymerizes cellulose of the lignocellulosic material into polysaccharides and/or oligosaccharides having an average chain length ranging from about 50 to about 750. In some embodiments, a cellulose hydrolytic microorganism depolymerizes cellulose of the lignocellulosic material into polysaccharides and/or oligosaccharides having an average chain length ranging from about 100 to about 500. In some embodiments, a cellulose hydrolytic microorganism depolymerizes cellulose of the lignocellulosic material into polysaccharides and/or oligosaccharides having an average chain length ranging from about 200 to about 400.

In some embodiments, any cellulose hydrolytic microorganism described herein can depolymerize cellulose of the lignocellulosic material to produce polysaccharides, oligosaccharides or mixtures thereof having any of the foregoing average chain lengths. In some embodiments, for example, brown rot fungi described herein can depolymerize cellulose of the lignocellulosic material to produce polysaccharides, oligosaccharides or mixtures thereof having any of the foregoing average chain lengths.

In some embodiments, degradation of lignin material by the lignin degrading fungus facilitates access to cellulose of the lignocellulosic material for the cellulose hydrolytic microorganism. As a result, the lignin degrading fungus or fungi and cellulose hydrolytic microorganism, in some embodiments, work in conjunction to increase cellulose depolymerization of the lignocellulosic material.

In some embodiments, a lignin degrading fungus and/or a cellulose hydrolytic microorganism is applied to a lignocellulosic material in any suitable manner known to one of skill in the art. In some embodiments, for example, a lignin degrading fungus and/or a cellulose hydrolytic microorganism is applied to a lignocellulosic material by liquid phase techniques. In some embodiments, a lignin degrading fungus and/or cellulose hydrolytic microorganism is applied to a lignocellulosic material by contacting the lignocellulosic material with a lignocellulosic material containing the lignin degrading fungus and/or cellulose hydrolytic microorganism.

Embodiments of methods described herein contemplate any combination of lignin degrading fungus or fungi and cellulose hydrolytic microorganisms. In some embodiments, for example, methods described herein contemplate any combination of white rot fungi of Table I with brown rot fungi of Table II and/or cellulose hydrolytic bacteria of Table III.

Moreover, in some embodiments of methods described herein, cellulose and/or hemicellulose of the lignocellulosic material can be further depolymerized by one or more cellulase enzymes into monomeric sugars, including various hexoses, pentoses or mixtures thereof. In some embodiments, cellulose of the lignocellulosic material is treated with one or more endocellulases, exocellulases, cellobiases, oxidative cellulases and/or cellulose phosphorylases. In some embodiments, for example, a cellulose of the lignocellulosic material can be further depolymerized with one or more exoglucanases, endoglucanases, $\beta$-glucosides and/or oxidative enzymes to produce glucose monomeric units.

In some embodiments, treatment of a lignocellulosic material with at least one lignin degrading fungus and at least one cellulose hydrolytic microorganism provides an increased amount of cellulose in a morphology for facile depolymerization by one or more cellulases into monomeric sugars. As a result, methods described herein, in some embodiments, can assist in realizing increased conversion of lignocellulosic biomass into monomeric sugars for various uses including feedstocks and ethanol production.

In another aspect, methods of producing ethanol are described herein. In some embodiments, a method of producing ethanol comprises providing a lignocellulosic material, degrading lignin of the lignocellulosic material with at least one fungus, hydrolyzing cellulose of the lignocellulosic material with at least one microorganism, further hydrolyzing the cellulose with one or more cellulase enzymes into one or more fermentable sugars and fermenting the one or more sugars into ethanol.

In some embodiments, lignin of the lignocellulosic material is selectively degraded by the at least one fungus. In some embodiments of methods of producing ethanol, the at least one fungus comprises a white rot fungus. In some embodiments, the at least one fungus comprises a plurality of fungi. The plurality of fungi, in some embodiments, comprises white rot fungi.

In some embodiments, the at least one cellulose hydrolytic microorganism of a method of producing ethanol comprises at least one fungus. In some embodiments, for example, a cellulose hydrolytic microorganism comprises a brown rot fungus. The at least one microorganism, in some embodiments, comprises a plurality of fungi. In some embodiments, a plurality of fungi serving as the cellulose hydrolytic microorganism comprises brown rot fungi. Alternatively, a microorganism, in some embodiments, comprises one or more cellulose hydrolytic bacteria. In some embodiments, the at least one microorganism comprises a combination of fungus and cellulose hydrolytic bacteria.

In some embodiments of producing ethanol, any lignin degrading fungus and cellulose hydrolytic microorganism described herein can be used.

In some embodiments of producing ethanol, a lignin degrading fungus is applied to the lignocellulosic material prior to application of the at least one cellulose hydrolytic microorganism. In some embodiments, the microorganism is applied to the lignocellulosic material prior to application of a lignin degrading fungus. In some embodiments, a lignin degrading fungus and a microorganism are applied to the lignocellulosic material simultaneously or substantially simultaneously.

In some embodiments of producing ethanol wherein a lignin degrading fungus is applied to the lignocellulosic material, the lignocellulosic material is sterilized or substantially sterilized prior to application of the at least one cellulose hydrolytic microorganism. In some embodiments, for example, a lignin selective white rot fungus is applied to the lignocellulosic material for a desired period of time. The lignocellulosic material is subsequently sterilized or substantially sterilized prior to application of a microorganism, such as a brown rot fungus, for the hydrolysis of cellulose of the lignocellulose material.

In some embodiments, the lignocellulosic material is not sterilized prior to application of the at least one microorganism such that the lignin degrading fungus and the cellulose hydrolytic microorganism exist simultaneously on the lignocellulosic material.

In some embodiments, a lignin selective fungus or fungi degrades at least a portion of lignin of the lignocellulosic material without degrading or substantially degrading cellulose of the lignin cellulosic material. In some embodiments, a lignin selective fungus or fungi degrades all or substantially all of the lignin of the lignocellulosic material without degrading or substantially degrading cellulose of the lignocellulosic material.

In some embodiments, degradation of the lignin provides increased access to the cellulose and/or hemicellulose of the lignocellulosic material for hydrolysis by the microorganism and one or more cellulase enzymes. Hydrolysis of cellulose by the microorganism and one or more cellulase enzymes, including those described herein, can produce sugars suitable for fermentation into ethanol by techniques known to one of skill in the art. In some embodiments of producing ethanol, monomeric sugars produced according to methods described herein comprise hexoses, pentoses and/or mixtures thereof. In some embodiments, hexoses comprise glucose, mannose or galactose or mixtures thereof. In some embodiments, pentoses comprise xylose or arabinose or mixtures thereof.

In another aspect, bioreactors for treating lignocellulosic material are described herein. In some embodiments, a bioreactor comprises a container for storing lignocellulosic material and apparatus for introducing at least one lignin degrading fungus and at least one cellulose-hydrolytic microorganism to the lignocellulosic material in the container. In some embodiments, a lignin degrading fungus and cellulose hydrolytic microorganism introduced to the lignocellulosic material through the apparatus of the bioreactor can comprise any lignin degrading fungus and cellulose hydrolytic microorganism described herein.

In some embodiments, a container of a bioreactor described herein has a volume sufficient to hold at least 1 ton of lignocellulosic material. In some embodiments, a bioreactor container has a volume sufficient to at least 2 tons or at least 3 tons of lignocellulosic material. In some embodiments, a bioreactor container has a volume sufficient to at least 4 tons or at least 5 tons of lignocellulosic material.

In some embodiments, apparatus for introducing at least one lignin degrading fungus to the lignocellulosic material comprises a fluid transport system with one or more injection points for liquid phase application of the at least one lignin degrading fungus. Similarly, in some embodiments, apparatus for introducing at least one cellulose hydrolytic microorganism to the lignocellulosic material comprises a fluid transport system with one or more injection points for liquid phase application of the at least one cellulose hydrolytic microorganism.

Moreover, in some embodiments, a bioreactor described herein further comprises one or more agitators for mixing or mechanically agitating the lignocellulosic material in the container. Additionally, in some embodiments, a bioreactor described herein comprises apparatus suitable for autoclaving or otherwise sterilizing the lignocellulosic material in the container, such as apparatus for steam treating the lignocellulosic material.

In some embodiments, a bioreactor described herein further comprises climate control apparatus for regulating the temperature and moisture content of the lignocellulosic material and/or surrounding environment. In some embodiments, a bioreactor comprises water spraying apparatus to control the moisture content of the lignocellulosic material as well as heating and cooling apparatus for controlling temperature of the lignocellulosic material and surrounding environment.

Embodiments of compositions and methods described herein are further illustrated by the following non-limiting examples.

EXAMPLE 1

Treatment of Lignocellulosic Material
A lignocellulosic material was treated in accordance with one embodiment of a method described herein as follows:
I. Fungal Isolates, Culture Conditions, and Wood Fresh cut *Liriodendron tulipifera* (Tulip Poplar) wood chips ($\approx 3\times 3\times 0.5$ cm) were collected from a hardwood lumber mill and stored at 4° C. until use. The wood was a mixture of earlywood and latewood chipped from duramen without orientation. The chips were visually inspected to verify the homogeneity of all the samples before treatment (defect wood removed). *Ceriporiopsis subvermispora* FP-90031-sp (a lignin-selective white rot fungus), and *Postia placenta* Mad-698-R (a brown rot fungus) were obtained from U.S.D.A. Forest Products Laboratory, Madison, Wis., USA. The fungi were independently cultured in malt extract agar (MEA) and incubated at 28° C. for 7-10 days. A fungal plug from the malt extract agar plate was then placed in 500 ml malt extract liquid medium and incubated at 28° C. for 7-10 days.

All treatments were conducted in triplicate. For each treatment, 1 gram (oven dry weight) of wood chips was placed in 20 ml scintillation vials and distilled water was added to increase moisture content to 70%. The loosely capped vials were then steam sterilized for 30 minutes. The malt extract liquid fungal cultures were vigorously shaken for one minute before use, and 0.2 ml was used to aseptically inoculate each wood chip treatment vial. The controls were also sterilized and 0.2 ml of media from the malt extract cultures was sterile filtered and added to each sterile control vial. The vials were then incubated for 30 days at 28° C. for optimal delignification and depolymerization. After the 30 day colonization period, the vials designated for two-stage biopulping treatment were steam sterilized for 30 minutes and then inoculated with the second fungal species, using the same inoculation volume and sterile media control as before. The two-stage treatment vials were then incubated for an additional 30 days at 28° C. The treatment vials were then oven dried 24 hours at 104° C.

A summary of the *Liriodendron tulipifera* treatment classes is provided in Table IV.

TABLE IV

*Liriodendron tulipifera* treatment classes

| Treatment | Stage 1 | Stage 2 |
|---|---|---|
| 1-Untreated/Sterile | Sterilize (30 min) | None |
| 2-Single Stage White Rot | Sterilize followed by application of *Ceriporiopsis subvermispora* FP-90031-sp | None |
| 3-Untreated/Sterile | Sterilize (30 min) | Sterilize (30 min) |
| 4-Single Stage Brown Rot | Sterilize followed by application of *Postia placenta* Mad-698-R | None |
| 5-Two Stage White Rot followed by Brown Rot | Sterilize followed by application of *Ceriporiopsis subvermispora* FP-90031-sp | Sterilize followed by application of *Postia placenta* Mad-698-R |
| 6-Two State Brown Rot followed by White Rot | Sterilize followed by application of *Postia placenta* Mad-698-R | Sterilize followed by application of *Ceriporiopsis subvermispora* FP-90031-sp |

II. Chemical Analysis

Gravimetric determination of Klason lignin content of the untreated/sterile controls and fungi treated samples were performed using previously described microanalytical techniques. (Yokohama et al., *Journal of Agricultural and Food Chemistry*, 50, 1040-1044; Yeh et al., *Journal of Agricultural and Food Chemistry*, 53, 1435-1439).

Klason lignin was prepared from extractive free wood meal. For each sample, 300 mg of oven dry weight wood and 3 mL of 72% sulfuric acid was placed in a 90 mL pressure tube. The sample was then stirred with a glass rod every 15 min for 60 min. The acid was then diluted to 4% concentration by addition of 84 mL of deionized water. The pressure tubes were then capped and autoclaved for one hour at 121° C., cooled overnight at 4° C., and filtered using a sintered glass filter (medium pore size). Acid insoluble lignin was washed with deionized water and dried at 104° C. before weighing. Klason lignin contents were recorded as a percentage of sample mass.

III. Enzymatic Hydrolysis

Enzymatic hydrolysis was performed on ground material (40 mesh particle size) from triplicate treatments and controls using a modified method outlined in Shi et al., *Biomass and Bioenergy*, 33, 88-96, 2009, including a 1:1.75 mixture of cellulase (22 FPU/g of substrate) (Celluclast 1.5 L, Sigma Co.) and β-glucosidase (Novozyme 188, Sigma Co.) and a 3% biomass loading volume (3 replicate samples and 3 replicate controls without enzyme per biopulping treatment). Samples were shaken at 50° C. for 72 hours then centrifuged for 10 minutes at 3000 rpm. Aliquots of supernatants were filtered a 0.22 μm filter. Samples were analyzed by HPLC using electrochemical detection and a Carbo-Pac10 carbohydrate column (Dionex) (Lee et al., *Journal of Bioscience and Bioengineering*, 106, 162-167). The mobile phase was 3 mM NaOH, which was circulated with a flow rate of 0.2 mL/min. Quantification and identification of peaks were performed using dilutions of arabinose, galactose, glucose, xylose, and mannose stock standards. All peaks eluted within 45 min. Glucose contents were normalized to controls without enzymes.

Figure 1:
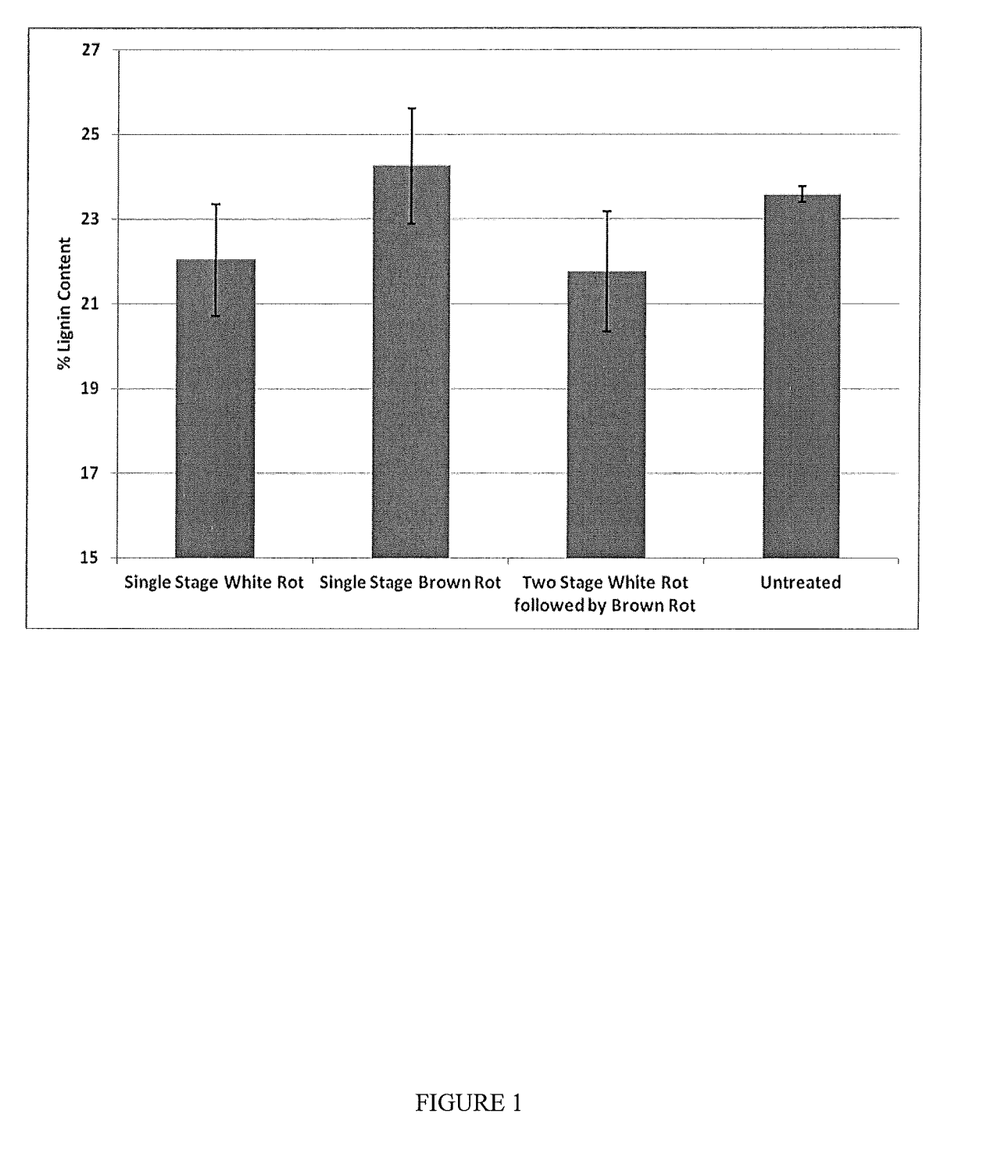
FIG. 1 illustrates the lignin content of untreated wood and wood treated with a lignin selective fungus according to some embodiments of methods described herein.

FIG. 1 illustrates the lignin content of wood of control treatment 1 in comparison with treatments 2, 4 and 5 of Table IV. The single stage white rot fungus of treatment 2 removed 1.5% of the lignin from the wood while the single stage brown rot fungus did not remove any lignin content from the wood. The two-stage process of treatment 5 removed 2% of the lignin from the wood. Error bars of FIG. 1=1 SE.

Figure 2:
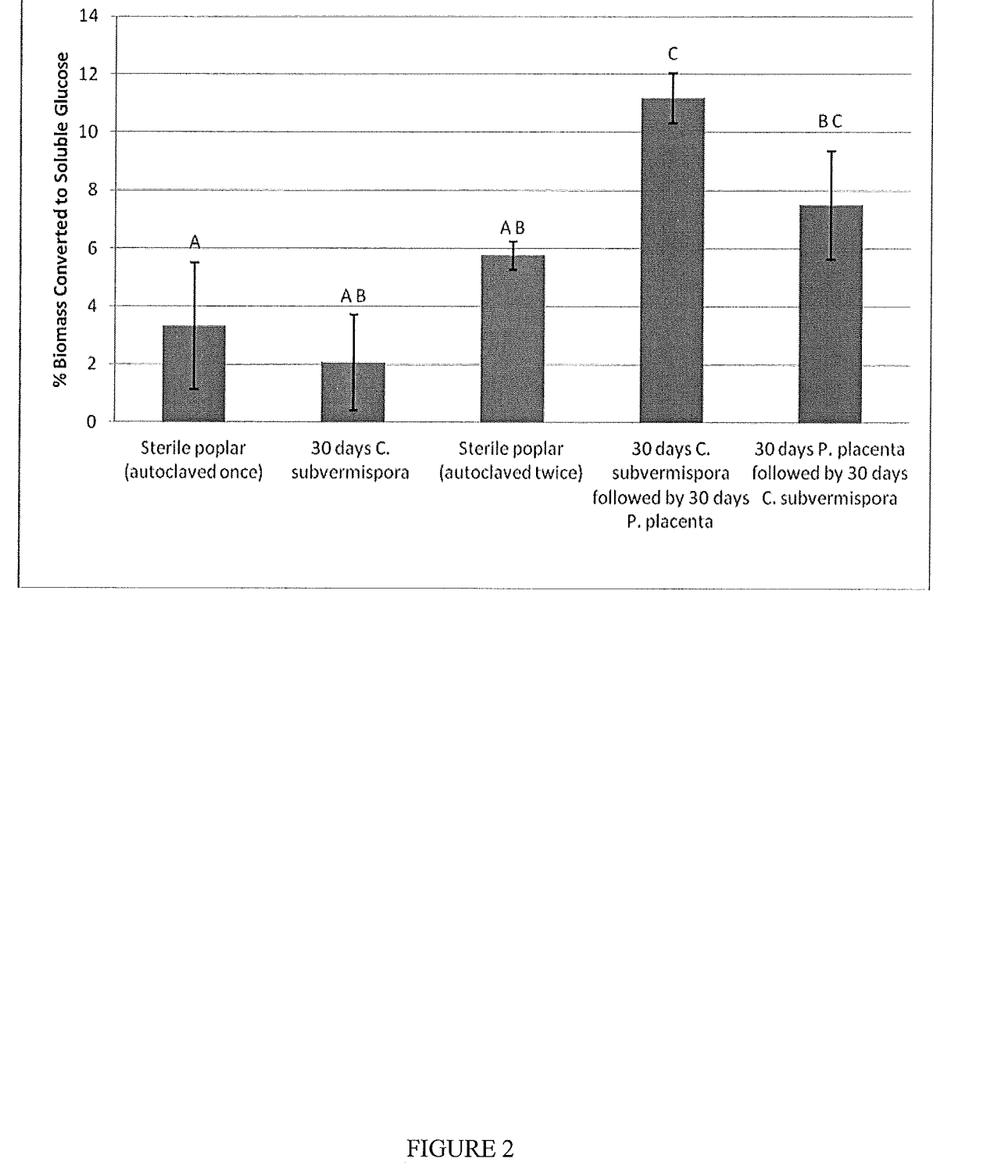
FIG. 2 illustrates percent lignocellulosic biomass converted to glucose according to methods described herein in comparison with other treatment methods.

FIG. 2 illustrates percent biomass converted to glucose according to treatments 1, 2, 3, 5 and 6 of Table IV. As illustrated in FIG. 2, the two stage process of treatment 5, according to one embodiment of a method described herein comprising application of a lignin degrading fungus followed by a cellulose hydrolytic fungus, resulted in the highest percent conversion of lignocellulosic biomass into soluble glucose. Moreover, the two stage process of treatment 6, according to one embodiment of a method described herein comprising application of a cellulose hydrolytic fungus followed by a lignin degrading fungus, resulted in the second highest percent conversion of lignocellulosic biomass to soluble glucose. Error bars of FIG. 2=1 SE.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A method of treating lignocellulosic material comprising:
   degrading lignin of the lignocellulosic material with *Ceriporiopsis subvermispora*; and
   hydrolyzing cellulose of the degraded lignocellulosic material with *Postia placenta*.

2. The method of claim 1, wherein the lignin is selectively degraded with the *Ceriporiopsis subvermispora*.

3. The method of claim 1, wherein at least 5 weight percent of the lignin is degraded by the *Ceriporiopsis subvermispora*.

4. The method of claim 1, wherein at least 10 weight percent of the lignin is degraded by the *Ceriporiopsis subvermispora*.

5. The method of claim 1, wherein the average chain length of the hydrolyzed cellulose is less than 1000 glucose units.

6. The method of claim 1, wherein the average chain length of the hydrolyzed cellulose ranges from 100 to 400 glucose units.

7. The method of claim 1, wherein the *Ceriporiopsis subvermispora* is applied to the lignocellulosic material prior to application of the *Postia placenta*.

8. The method of claim 7 further comprising
   sterilizing the lignocellulosic material prior to application of the *Postia placenta*.

9. The method of claim 1 further comprising hydrolyzing the cellulose with one or more cellulases to produce monomeric sugars.

10. The method of claim 1, wherein the *Postia placenta* is applied to the lignocellulosic material prior to application of the *Ceriporiopsis subvermispora*.

11. The method of claim 1, wherein the *Ceriporiopsis subvermispora* and the *Postia placenta* are applied to the lignocellulosic material simultaneously.

12. The method of claim 1 further comprising hydrolyzing hemicellulose of the degraded lignocellulosic material with the *Postia placenta*.

13. The method of claim 8, wherein the white rot fungus is *Ceriporiopsis subvermispora*.

14. The method of claim 13, wherein the brown rot fungus is *Postia placenta*.

* * * * *